United States Patent [19]

Signorini et al.

[11] 4,408,074
[45] Oct. 4, 1983

[54] PROCESS FOR PREPARING 1-(3,5-DIMETHOXY-4-HYDROXY PHENYL)-2-(N-METHYLAMINO) ETHANOL HYDROCHLORIDE

[75] Inventors: Massimo Signorini; Attilio Trebbi, both of Baranzate; Luigi Molteni, Malnate, all of Italy

[73] Assignee: Dr. Lo. Zambeletti S.p.A., Milan, Italy

[21] Appl. No.: 317,517

[22] Filed: Nov. 2, 1981

[30] Foreign Application Priority Data

Nov. 28, 1980 [IT] Italy ............................... 26293 A/80

[51] Int. Cl.$^3$ .............................................. C07C 91/16
[52] U.S. Cl. .................................. 564/361; 260/511; 564/343; 564/344; 564/356; 564/357; 568/764; 568/765
[58] Field of Search ............... 564/361, 363, 357, 356

[56] References Cited

U.S. PATENT DOCUMENTS 3,642,896  2/1972  Collin .............................. 564/343 X

*Primary Examiner*—Robert V. Hines
*Attorney, Agent, or Firm*—Bucknam and Archer

[57] ABSTRACT

A process for preparing 1-(3,5-dimethoxy-4-hydroxy phenyl)-2-(N-methylamino) ethanol hydrochloride is described by reacting 2,6-dimethoxyphenol with anhydrous chloral in the presence of a catalyst, hydrolyzing 1-(3,5-dimethoxy-4-hydroxyphenyl)2,2,2-trichloro ethanol and subsequently isolating the 3,5-dimethoxy-4-hydroxyphenyl glyoxal thus obtained; finally, this compound, in the form of the bisulfite, is directly converted to the desired product by amination with methylamine in the presence of hydrogen with a hydrogenation catalyst and the final product is converted into the hydrochloride.

5 Claims, No Drawings

PROCESS FOR PREPARING 1-(3,5-DIMETHOXY-4-HYDROXY PHENYL)-2-(N-METHYLAMINO) ETHANOL HYDROCHLORIDE

DESCRIPTION OF THE INVENTION

The present invention relates to a novel process for preparing 1-(3,5-dimethoxy-4-hydroxy phenyl)-2-(N-methylamino) ethanol hydrochloride (I). This compound is a pharmaceutical endowed with remarkable therapeutic effectiveness because of its antihypotensive properties (see e.g. the British Pat. No. 1,145,637 in the name of the same applicant as this application).

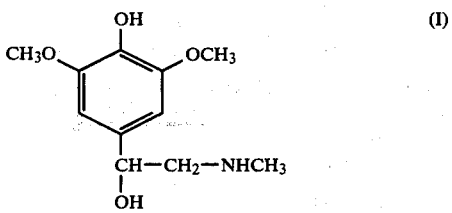

In the applicant's British Pat. No. 1,145,637 there is disclosed a process for preparing the compound (I), which comprises condensing halogenoketones of formula (II) with methylamine and catalytically reducing the aminoketone (III) thus obtained, according to the following reaction scheme:

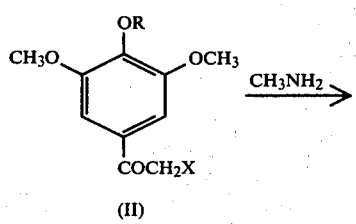

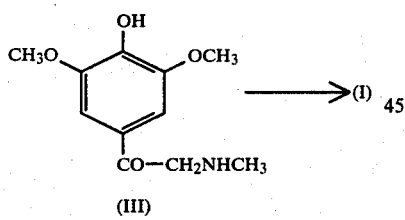

wherein R is either H or CH₃CO and X is either Cl or Br. ω-chloro-acetyl-acetosyringone (II, wherein R=CH₃CO and X=Cl) can be synthesized by reacting the chloride of the acetylsyringic acid (IV) with diazomethane and decomposing with hydrochloric acid the diazoketone (V) thus obtained (see British Pat. No. 1,145,637), according to the following reaction scheme:

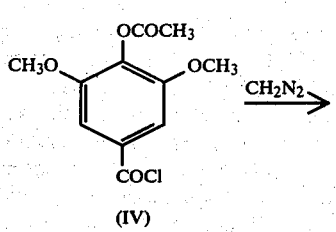

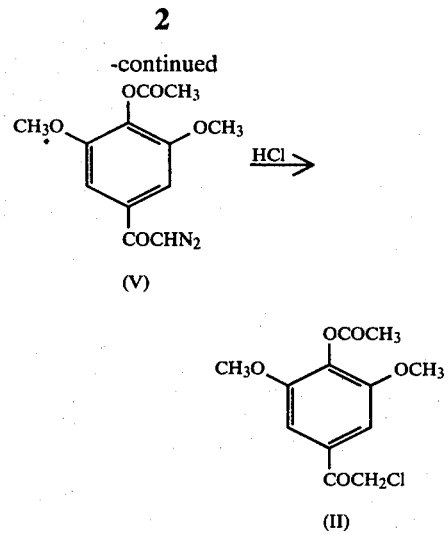

It is apparent that this preparation method (which even when carried out on a laboratory scale does not afford particularly high yields) is not feasible on an industrial scale, mostly because of the use of diazomethane, an extremely toxic gas which is liable to explode not only by heating, but also by mere contact with which are not perfectly smooth surfaces.

According to a further process (disclosed in the Dutch Pat. No. 7307100), the ω-chloro-acetosyringone (II, wherein R represents hydrogen and X represents chlorine) can be obtained by chlorinating with sulfuryl chloride α-(3,5-dimethoxy-4-benzyloxy-benzoyl) methyl acetate (VI), dissolved in glacial acetic acid, and subsequently treating the intermediate (VII) thus obtained with concentrated hydrochloric acid. During this treatment the following take place at the same time: a hydrolysis, a debenzylation and a decarboxylation which lead to the aforementioned ω-chloro-acetosyringone. The reaction scheme is the following:

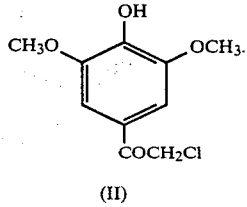

(II)

The foregoing process, although practical on an industrial scale, presents serious drawbacks, first because of the burdensome problems connected with the neutralisation and disposal of mother liquors (consisting of acetic acid and hydrochloric acid) and because of the removal of sulfur dioxide which is set free in equimolar amounts during the chlorination reaction with sulfuryl chloride. Moreover, the overall reaction yield is far from the theorical value, and this becomes even more serious because in the conversion of compound (VI) into ω-chloroacetosyringone (II) a sharp decrease in molecular weight takes place.

According to another synthesis, disclosed in the British Pat. No. 1,188,480 in the name of the same applicant as this application, ω-bromo-acetyl acetosyringone (II, wherein R represents acetyl and X represents bromine) can be prepared from 2,6-dimethoxy-1-acetoxybenzene by Fries transposition with aluminium chloride in nitrobenzene, acetylation of the acetosyringone (IX) thus obtained and deacetylating bromination. This synthesis pathway can be summarized as follows:

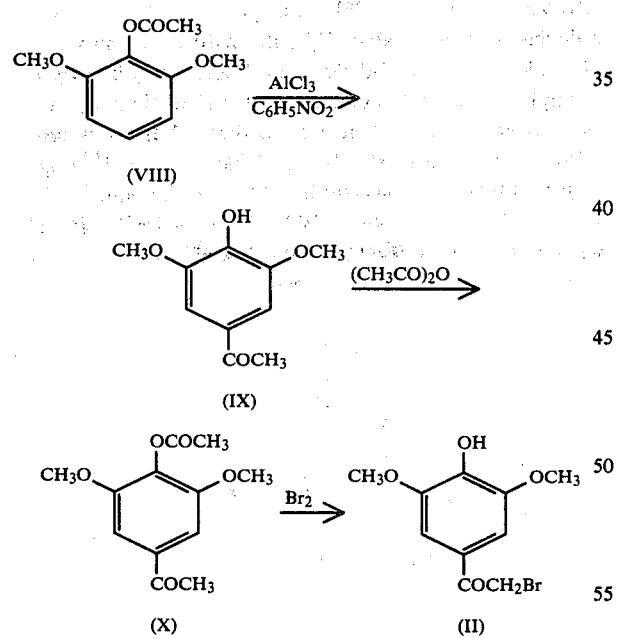

Several drawbacks, however, accompany this method. The use of anhydrous aluminium chloride which is very moisture-sensitive; the use of bromine, an extremely reactive element; the use, as solvent, of nitrobenzene which, because of its very high toxicity, needs strict control with respect to ecological and pollution requirements. In addition to the foregoing, also the poor yield of both the Fries transposition (44%) and the subsequent reaction between bromoacetosyringone and methylamine should be considered. Indeed, this latter reaction is less satisfactory than the similar reaction between chloroacetosyringone and methylamine, because of the excessive reactivity of bromine which leads to formation of considerable amounts of side-products.

All the previous syntheses pathway share a common drawback, i.e. they all require preparing, centrifuging, drying and reacting ω-halogeno-acetophenones, which are highly irritant above all to the eyes and the nasal mucous membrane as well as dangerous in case of prolonged exposure and subjective hypersensitivity.

It has now been found that 1-(3,5-dimethoxy-4-hydroxyphenyl)-2-(N-methylamino) ethanol (I) can be prepared in a particularly advantageous way in view of both high reaction yields and the absence of irritant, toxic, dangerous and polluting reactants and solvents, according to the synthesis illustrated hereinbelow:

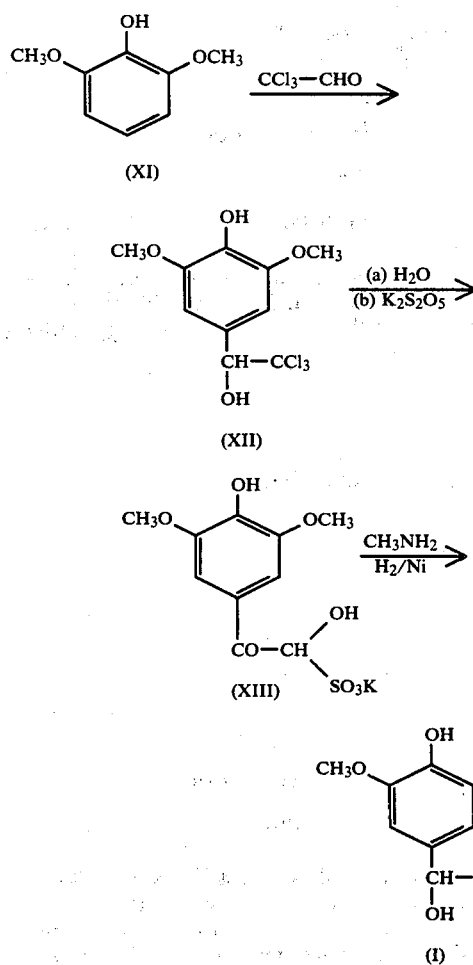

The first step of the process according to the invention comprises, therefore, condensing 2,6-dimethoxyphenol (XI) and anhydrous chloral, thus obtaining 1-(3,5-dimethoxy-4-hydroxyphenyl)-2,2,2-trichloro ethanol (XII). In "Pharmazeutische Zentralhalle für Deutschland, 92, 237–241 (1953)" a similar reaction between guaiacol and chloral hydrate is disclosed.

It has been found, however, that in the reaction conditions disclosed in the foregoing article, the reaction between (XI) and chloral hydrate does not take place at all, or—by prolonging the reaction times and in the presence of a large excess of chloral hydrate—leads to a highly impure product (XII) with very low yields (18-20%).

On the other hand, it has unexpectedly been found that by carrying out the reaction with anhydrous chloral, the reaction takes place smoothly with yields higher than 80%. As catalysts, alkali metal phosphates and carbonates are suitably added. 1-(3,5-dimethoxy-4-hydroxyphenyl)-2,2,2-trichloroethanol (XII), obtained as a pure and crystalline compound, is then boiled in water and potassium 1-hydroxy-2-keto-2-(3,5-dimethoxy-4-hydroxyphenyl)-ethanesulfonate (XIII) is precipitated out from the solution thus obtained with potassium metabisulfite.

The third and last step of the process according to the invention consists of the reducing amination of the compound (XIII) and is carried out with methylamine and Raney nickel (or other hydrogenation catalysts), initially at 1-10 atmospheres and room temperature and subsequently raising the temperature to 60°-80° C. and the pressure to 50-60 atmospheres; these last temperature and pressure values can be adopted, on the other hand, since the beginning of this process step. The product is then converted into the hydrochloride.

Alternatively, the bisulfite compound (XIII) can be subjected first to reducing amination with methylamine in the presence of Raney nickel at a pressure of 1-10 atmospheres of hydrogen and at room temperature. The compound ω-methylamino-3,5-dimethoxy-4-hydroxyacetophenone (III) thus obtained from the reaction is then hydrogenated to 1-(3,5-dimethoxy-4-hydroxyphenyl0-2-N-methylamino ethanol (I) and finally converted into the hydrochloride. In order to carry out the reduction the most conventional hydrogenation catalysts (Raney nickel, palladium on carbon, platinum oxide, etc.) can be used.

The following examples illustrate the invention without limiting its scope.

EXAMPLE 1

(a)

1-(3,5-Dimethoxy-4-hydroxyphenyl)-2,2,2-trichloroethanol (XII)

47 grams of anhydrous chloral and 50 grams of 2,6-dimethoxyphenol were introduced in a reactor thermostated at 45° C. Upon obtaining a homogeneous solution, a mixture of 6.4 grams of potassium carbonate and 1.6 grams of sodium phosphate was added thereto portionwise under stirring in a 3-hour period. At the end of the addition, the mixture was left under stirring at the same temperature until the mixture thickened. The stirring was stopped and the mixture was left stand overnight at 45° C. The mixture was kneaded a long time in water and filtered. A yellow-reddish solid product was obtained, which was crystallized from aqueous ethanol. Yield: 82 grams (83.9% calculated on dimethoxyphenol). Analysis: chlorine 34.7% theoretical 35.27%), melting point 160°-162° C.; purity 97.5% (GC).

(b) Potassium 1-hydroxy-2-keto-2-(3,5-dimethoxy-4-hydroxyphenyl)-ethanesulfonate (XIII)

70 grams of the compound (XII) were suspended in 2 liters of water and refluxed for about 20 hours. The dark solution thus obtained was cooled, filtered on charcoal, neutralized with potassium carbonate and finally 42 grams of potassium metabisulfite were added thereto. The solution was concentrated under vacuum to one half of its initial volume, until a crystalline precipitate began to form. The mixture was left overnight at 4° C., and the precipitate was filtered off. Yield: 66 grams (86%); melting point 215°-220° C. (decomposition); Cl=absent; S 9.5% (theoretical 9.7%).

(c)

1-(3,5-Dimethoxy-4-hydroxyphenyl)-2-methylaminoethanol hydrochloride (I)

56 grams of the bisulfite compound (XIII) were dissolved in 250 mls. of a 40% $CH_3NH_2$ aqueous solution to which 50 mls. of water were added. To the dark red solution about 12 grams of Raney nickel were added. The mixture was then hydrogenated at an initial pressure of 60 atmospheres of hydrogen, heating up to 60° C. After the theoretical amount of hydrogen was absorbed, the catalyst was filtered off and the solution was concentrated under reduced pressure, until a thick suspension was obtained which after cooling was filtered with suction. The crystalline product thus obtained was washed with water, then (in order to convert it into hydrochloride) was suspended in 100 mls. of water and treated with concentrated HCl until pH 1-2 was reached. The solution was treated with animal charcoal, filtered and evaporated under vacuum until incipient crystallization, then added under stirring to 150 mls. of acetone. The colorless crystals thus obtained were filtered via the pump and washed with acetone. 39.1 grams of the hydrochloride of the compound (I) were obtained, melting point 175° C. Analysis: Cl found 13.48% (calculated 13.5%).

EXAMPLE 2

(a)

ω-Methylamino-3,5-dimethoxy-4-hydroxyacetophenone (III) hydrochloride 56 grams of the bisulfite compound (XIII) (obtained as shown in Example 1 b)) were dissolved in 250 mls. of 40% aqueous monomethylamine and 50 mls. of water. The dark red solution was hydrogenated over about 10 grams of Raney nickel at room temperature and pressure, until the theoretical amount of hydrogen was absorbed. The catalyst was filtered off and the solution was concentrated under vacuum until a thick suspension was obtained. The mixture was cooled and filtered, thus obtaining an amorphous precipitate which was suspended in water and filtered once again. The ketoamine was converted into hydrochloride by suspending it in about 3 volumes of methanol and acidifying the suspension with ether saturated with hydrochloric acid. Yield: 36 grams of hydrochloride. Melting point 235° C., Cl 13.3% (theorical 13.6%)

(b)

1-(3,5-Dimethoxy-4-hydroxyphenyl)-2-methylamino ethanol (I) hydrochloride 36 grams of the hydrochloride (III) were dissolved in 180 mls. of water, and the solution was hydrogenated at 60° C. and 60 atmospheres on 4 grams of Raney nickel. After the hydrogenation was terminated, the catalyst was filtered off and the solution was concentrated under vacuum until incipient crystallization. The suspension was poured under stirring into 150 mls. of acetone. The crystalline white powder thus formed was filtered off. Yield: 29 grams. Melting point 175° C., Cl 13.45% (theorical 13.6%).

What is claimed is:

1. A process for manufacturing 1-(3,5-dimethoxy-4-hydroxy phenyl)-2-(N-methylamino) ethanol hydrochloride which comprises:
   (a) condensing 2,6-dimethoxy phenol with anhydrous chloral, thus obtaining 1-(3,5-dimethoxy-4-hydroxy phenyl)-2,2,2-trichloro ethanol;
   (b) heating an aqueous solution of said 1-(3,5-dimethoxy-4-hydroxyphenyl)-2,2,2-trichloro ethanol with an alkali metal or an alkaline-earth metal metabisulfite thus obtaining an alkali metal or an alkaline-earth metal 1-hydroxy-2-keto-2-(3,5-dimethoxy-4-hydroxyphenyl) ethanesulfonate in which M is an alkali or alkaline earth metal; and
   (c) subjecting to amination under reducing conditions with methylamine in the presence of hydrogenation catalysts said compound followed by reaction with hydrochloric acid:

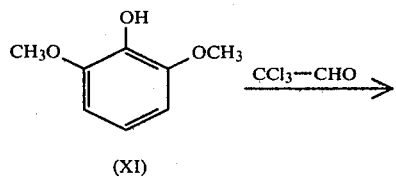

(XI)

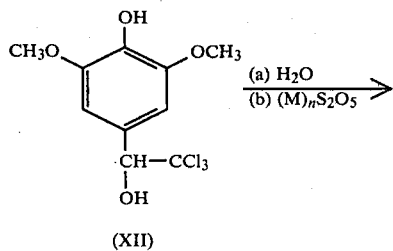

(XII)

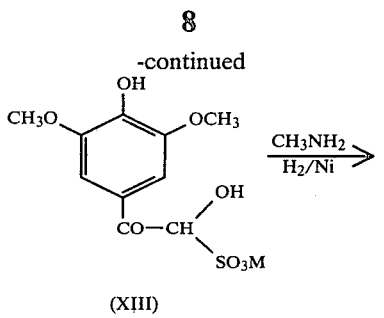

(XIII)

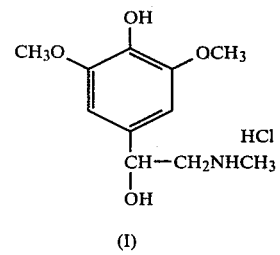

(I)

wherein n = 1 or 2.

2. The process according to claim 1 wherein Raney nickel is used as hydrogenation catalyst.

3. The process according to claims 1 or 2 wherein the amination is carried out at a pressure of about 50–60 atmospheres of hydrogen and at 60°–80° C.

4. The process of claim 1 wherein amination is carried out in two steps, first by converting said compound from step (b) to the product ω-methylamino-3,5-dimethoxy-4-hydroxyacetophenone and then hydrogenating said product in the form of the hydrochloride to 1-(3,5-dimethoxy-4-hydroxyphenyl)-2N-methylamino ethanol hydrochloride.

5. The process according to claim 1 wherein M is an alkali metal and n = 1.

* * * * *